United States Patent
Ray

(10) Patent No.: US 6,309,887 B1
(45) Date of Patent: Oct. 30, 2001

(54) FILTER PAPER TREATMENT FOR IMPROVED DIAGNOSTIC ASSAYS

(75) Inventor: Robert A. Ray, Stuart, FL (US)

(73) Assignee: FlexSite Diagnostics, Inc.

( * ) Notice: Subject to any disclaimer, the term of this patent is extended or adjusted under 35 U.S.C. 154(b) by 0 days.

(21) Appl. No.: 09/238,114

(22) Filed: Jan. 27, 1999

Related U.S. Application Data

(60) Provisional application No. 60/072,636, filed on Jan. 27, 1998.

(51) Int. Cl.$^7$ .................................................. G01N 33/72
(52) U.S. Cl. ........................... 436/67; 436/66; 436/69; 436/169; 422/56; 422/73
(58) Field of Search ................................. 436/63, 66, 67, 436/69, 164, 169, 177, 178; 422/55, 56, 68.1, 73, 99, 101

(56) References Cited

U.S. PATENT DOCUMENTS

| | | | |
|---|---|---|---|
| 3,672,351 | * 6/1972 | Ubersax et al. | 600/371 |
| 4,219,336 | * 8/1980 | Guthlein et al. | 436/66 |
| 4,277,249 | 7/1981 | Broughton | 436/86 |
| 4,299,812 | 11/1981 | Coombes | 436/500 |
| 4,687,000 | * 8/1987 | Eisenhardt et al. | 600/573 |
| 4,774,192 | 9/1988 | Terminiello et al. | 436/530 |
| 4,790,979 | 12/1988 | Terminiello et al. | 422/56 |
| 4,816,224 | 3/1989 | Vogel et al. | 422/55 |
| 5,204,267 | 4/1993 | Sangha et al. | 436/14 |
| 5,378,431 | * 1/1995 | Vogler et al. | 422/73 |
| 5,415,758 | 5/1995 | Comeau | 204/462 |
| 5,427,953 | 6/1995 | Yee | 436/74 |
| 5,432,097 | 7/1995 | Yourno | 436/175 |
| 5,460,057 | 10/1995 | Østrup | 73/864.81 |
| 5,496,626 | 3/1996 | Hamajima et al. | 442/412 |
| 5,508,200 | 4/1996 | Tiffany et al. | 436/44 |
| 5,516,487 | 5/1996 | Rosenthal et al. | 422/55 |

FOREIGN PATENT DOCUMENTS

05273204 * 10/1993 (JP) .

OTHER PUBLICATIONS

Illnait et al. *Rev. Cienc. Biol.* (Havana), vol. 16, No. 2, pp. 207–212. (CA abstract No. 106:134 624), 1985.*

Hawley *The Condensed Chemical Dictionary—10th edition*, p. 431, 1981.*

Guthrie, R., et al., A Simple Phenylalanine Method for Detecting Phenylketonuria in Large Populations of Newborn Infants, Pediatrics 32(3): 338–343 (1963).

Eross, J., et al., Colorimetric measurement of glycosylated protein in whole blood, red blood cells, plasma and dried blood, Ann. Clin. Biochem., 21: 477–483 (1984).

Little, et al., Collection of Blood on Filter Paper for Measurement of Glycated Hemoglobin by Affinity Chromatography, Clin. Chem. 42(5): 869–871 (1986).

Voss, et al., Stability and Accuracy Evaluation of a Capillary Collection System for Hemoglobin A1c Specimens, Clin. Chem. 37(6): 988, Abstract 0373 (1991).

Voss, et al., Evaluation of Capillary Collection System HbA1c Specimens, Diabetes Care 15(5): 700–701 (1992).

Jeppsson et al., Capillary Blood on Filter Paper for Determination of HbA1c by Ion Exchange Chromatography, Diabetes Care 19(2): pp. 142–145 (1995).

Niederau, et al., Evaluation of a Non–Liquid Transportable Device for Capillary Blood Suitable for HbA1c Determination, Clin. Chem. 42(6): 167, Abstract 0297 (1996).

Little, et al., Filter Paper Collection of Blood for Measurement of HbA1c Immunoassay, Clin. Chem. 42(6): 193, Abstract 0404 (1996).

Marsden, et al., The Comparative Performances of Whatham BFC 180 and S&S 903 Filter Papers in Newborn Screening Assays for Immunoreactive Trypson, 17–OHP and Galactose, Third Meeting of the International Society for Neonatal Screening and the 12th National Neonatal Screening Symposium, Boston, Massachusetts (Oct. 21–24, 1996).

Vohra, et al., Efficacy of New Filter Paper in a State Newborn Screening Program, Third Meeting of the International Society for Neonatal Screening and the 12th National Neonatal Screening Symposium, Boston, Massachusetts (Oct. 21–24, 1996).

Duddy, et al., The Evaluation of Whatman BFC180 Blood Collection Paper Against Two Alternative Products, Third Meeting of the International Society for Neonatal Screening and the 12th National Neonatal Screening Symposium, Boston, Massachusetts (Oct. 21–24, 1996).

* cited by examiner

*Primary Examiner*—Maureen M. Wallenhorst
(74) *Attorney, Agent, or Firm*—Akerman Senterfitt

(57) ABSTRACT

Filter paper absorbed with a solution of anticoagulant, e.g., ethylene diamine tetra-acetic acid (EDTA), then dried, useful for collection of a blood sample for analysis of hemoglobin or a hemoglobin fraction in the sample showed higher precision in standard assays than untreated filter paper. Methods of using the anticoagulant-treated filter paper are also described.

12 Claims, No Drawings

FILTER PAPER TREATMENT FOR IMPROVED DIAGNOSTIC ASSAYS

CROSS REFERENCE TO RELATED APPLICATIONS

This application claims the benefit of U.S. Provisional Application No. 60/072,636, filed Jan. 27, 1998.

STATEMENT REGARDING FEDERALLY SPONSORED RESEARCH OR DEVELOPMENT (Not Applicable)

BACKGROUND OF THE INVENTION

1. Field of the Invention

This invention relates to the general area of remote site blood sample collection for medical diagnostic tests. More specifically, the invention relates to a improved filter paper for collecting a blood sample for higher precision analysis of hemoglobin or a hemoglobin fraction.

2. Description of Related Art

Filter paper has been used for more than 20 years as a means of gathering samples of blood, especially from newborns, for the purpose of identifying or measuring specific components in the blood in screening for congenital metabolic disorders, e.g., phenylketonuria (PKU). Although PKU screening has been one of the most common applications of blood collection on filter paper, many other applications have been in use, including the use of filter paper for collecting samples to test for blood components associated with thyroid dysfunction or in monitoring diabetic conditions. There are numerous papers in the scientific literature describing these testing methods. Although certain of these publications relate to characteristics of the filter paper itself, e.g., precision, lot-to-lot variations, and variability of results due to contamination of the filter paper used, most of the publications in the scientific literature focus on the methods employing a filter paper.

In 1984, a research paper was published on the use of filter paper for collecting blood samples for the purpose of measuring total glycohemoglobin. Eross, et al. (1984) Ann. Clin. Biochem. 21:477–483. Glycohemoglobin refers to the glycosylated state of hemoglobin resulting from glucose entering the red blood cell. Measurement of glycohemoglobin is extremely important in metabolic control of diabetics. Although blood glucose levels can fluctuate during the course of the day, relative to eating, medication, exercise, or other factors, glycohemoglobin levels are not so acutely affected. Thus, by measuring glycohemoglobin rather than glucose directly, a more accurate or more constant reading of blood glucose levels can be determined. Certain improvements to the total glycohemoglobin assay, which have been described in the scientific literature, have been achieved by modifying the filter paper used in the glycohemoglobin assay. Specifically, pretreatment of the filter paper with an enzyme, e.g., glucose oxidase, was used to reduce the glucose concentration in a blood sample being tested for total glycohemoglobin concentrations by Eross and by Little, et al. (1986) Clin. Chem. 32(5):869–871. The presence of glucose in the blood sample can cause an undesirable increase in glycohemoglobin concentrations compared to actual levels. A glycohemoglobin assay product using filter paper treated with glucose oxidase has been commercialized and was marketed under the trade name Self-Assure™, FlexSite Diagnostics, Palm City, Fla.

Although the use of a glucose oxidase-treated filter paper in measuring total glycohemoglobin has been described, such use has only been described in relation to affinity chromatography assays for total glycohemoglobin. Recently, methods have been introduced to measure a specific fraction of total glycohemoglobin, the so-called $HbA_{1c}$ fraction, Glucose glycates hemoglobin protein at a number of amino acid sites. About half of the glycation occurs at the N-terminal valine of the beta chain of hemoglobin. This glycation product is designated $HbA_{1c}$. Antibody based methods for $HbA_{1c}$ have proved to be more specific than total glycohemoglobin methods. Thus, glucose present in the blood gives much larger errors in affinity chromatography methods for measuring total glycohemoglobin in dried blood spot than in an alternative method using an antibody assay, e.g., immunoprecipitation assays. Little, et al. (1996) Clin. Chem 42 (6): S193, showed that glucose present in a blood sample causes little interference in measuring the $HbA_{1c}$ fraction of glycohemoglobin using an antibody-based assay.

Two filter paper manufacturers, namely, Schleicher & Schuell (Keene, N.H., USA) and Whatman (Fairfield, N.J., USA) have devoted considerable commercial effort to refining certain of their filter paper products for application to dried blood spot methods, including glycohemoglobin testing. These refinements focus on consistency of the paper but not on treatment of the filter paper with various reagents. To date, it is not known to treat filter paper with a reagent other than glucose oxidase methods, according to Eross or Little, for use in a total glycohemoglobin assay.

In addition, it is not known that a treatment of the filter paper with a specific reagent can result in an improved assay for the $HbA_{1c}$ fraction of total glycohemoglobin by an antibody method. It is expected that when blood is applied to filter paper from a finger stick that coagulation will occur, thus binding the red blood cells into the clot matrix. It is further expected that when the blood is re-dissolved from the dried blood spot that coagulated blood will be more difficult to re-dissolve than un-coagulated blood, resulting in lower Hb concentrations in standard assays. Treatment with an anticoagulant of a filter paper used in an assay for measuring glycohemoglobin has not been heretofore described.

SUMMARY OF THE INVENTION

The subject invention concerns treatment of filter paper used for dried blood spot sample collection. More specifically, the subject invention concerns treatment of the filter paper with an anticoagulant, e.g., ethylenediamine tetra-acetic acid (EDTA), which results in easier dissolution of the dried blood spot compared to untreated filter paper, in the analysis of $HbA_{1c}$ and more direct comparison to EDTA anticoagulated venipuncture samples. The use of EDTA treated filter paper has the additional advantage of allowing exact comparison studies between freshly gathered finger stick blood applied to EDTA treated filter paper and larger quantities of veni-puncture blood collected in EDTA collection tubes. If EDTA were not used on the filter paper, the EDTA anti-coagulated veni-puncture samples might give different results in correlation studies with dried blood spots on untreated paper.

Thus, it is an object of the subject invention to provide an improved method and material for assaying components from dried blood samples collected on filter paper.

It is another object of the invention to provide an improved method and material for eluting dried blood samples collected on filter paper for purposes of assaying components in the blood sample.

It is yet another object of the invention to provide an improved material and method for assaying glycohemoglobin, or $HbA_{1c}$, in a dried blood sample collected on filter paper. Specifically, it is an object of the invention to provide an improved assay for measuring the $HbA_{1c}$ function of glycohemoglobin in blood by collecting a blood sample to be assayed for that component onto a filter paper which has been pre-treated with an anticoagulant, e.g. EDTA.

These, and other objects of the invention achieved by an absorption material which comprises filter paper and a chelating agent. The filter is adapted to collect a liquid biological sample, and the chelating agent is contained within the filter paper to prevent the liquid biological sample from coagulating. The filter paper is preferably cellulose based and collects approximately 20–30 $\mu$l of the biological sample.

The liquid biological sample to be collected is preferably blood, and the component of interest is glycohemoglobin or a $HbA_{1c}$ fraction of total glycohemoglobin. When blood is collected, the preferable chelating agent is ethylenediamine tetra-acetic acid (EDTA) or possibly citric acid. If ethylenediamine tetra-acetic acid is the chelating agent, the EDTA is preferably present in a quantity of at least 5 $\mu$g/20 $\mu$l of blood collectable by the filter paper to prevent coagulation of the blood; however, most preferably the EDTA should be present in a quantity of at least 10 $\mu$g/20 $\mu$l of blood collectable by the filter paper to further increase the precision of the assay to be performed on the sample.

A method for assaying a component of interest in a liquid biological sample is also disclosed which comprises the steps of providing a material for absorbing the biological sample comprising the component of interest; applying a chelating agent to the material for preventing the liquid biological sample from coagulating; applying the biological sample to the material; and, assaying the component in the biological sample. An additional step is drying the biological sample onto the material, and the drying step can be accomplished by heating the material at approximately 45° Celsius for approximately twenty-four hours.

DETAILED DESCRIPTION OF THE INVENTION

The subject invention comprises a pre-treated filter paper for use in glycohemoglobin ($HbA_{1c}$) assays typically used for monitoring average glucose levels in diabetic patients. In the course of development work, filter paper used in $HbA_{1c}$ assays was treated with ethylene diamine tetra-acetic acid (EDTA), which, unexpectedly, was found to decrease the hemoglobin (Hb) concentrations in samples dried overnight before HbA1c measurement. The precision of the eluted Hb value, determined as consistency of the values for replicate samples, was improved over that from untreated filter paper.

EDTA is a chelating agent which is routinely added to liquid blood samples to prevent them from coagulating. Although the use of EDTA as an anticoagulant has been routinely used for years with liquid blood samples, it is not known to be used for dried blood samples. When samples were heated for 2 days at 45° C. to simulate aging for 5–10 days (typical transport time, e.g., via U.S. Mail, for samples collected remotely and sent to a laboratory for analysis) at ambient temperature, similar results were obtained. The presence of the anticoagulant on the filter paper can further be advantageous for facilitating elution of dried blood from the filter paper on which a blood sample was collected.

The subject invention further comprises a method for an improved Hb or $HbA_{1c}$ assay. The subject method comprises applying a solution of anticoagulant to a filter paper used for collecting a blood sample, wherein the anticoagulant solution is of a concentration and amount sufficient to prevent coagulation of the volume of blood collected. Preferably, the anticoagulant solution is absorbed onto the filter paper and is allowed to dry prior to use of the filter paper for blood sample collection. The filter paper used can be cellulose or glass fiber, as is readily known in the art and commercially available. Preferably, the filter paper is cellulose based. Such cellulose filter papers useful in accordance with the subject invention are available from Schleicher & Schuell (Keene, N.H., USA) and Whatman (Fairfield, N.J., USA).

Anticoagulant used for the subject invention can be any known anticoagulant, for example, EDTA, citric acid, or the like. Such anticoagulants are commercially available. Typically, the anticoagulant is provided as a powder, dissolved in water or a buffer to form an aqueous solution comprising the anticoagulant. The anticoagulant should be present in at least amounts which are effective to prevent coagulation of blood. For example, for EDTA, it must be present in a quantity of at least 5 $\mu$g/20 $\mu$l (3.8 mM) of blood. Preferably, EDTA is present in a quantity of 10 $\mu$g/20 $\mu$l (7.7 mM) of blood. The 3.8 mM quantity of EDTA is referred to herein as "1×"; the 7.7 mM quantity is herein referred to as "2×" concentration. A blood volume collected by the filter paper method is normally about 20 $\mu$l–30 $\mu$l.

The filter paper having anticoagulant absorbed and dried thereon can be used to collect a blood sample and the glycohemoglobin assay carried out, according to standard and accepted procedures, or the manufacturer's instructions. The blood sample can be collected by placing a sample, e.g., a blood spot (typically 1–5 drops) from a finger stick using a standard lancet The following examples illustrate objectives, embodiments, and procedures, including the best mode, for practicing the present invention. However, the invention is not limited or restricted to the examples presented. Amounts are provided as volume per volume or weight per weight values unless otherwise indicated.

EXAMPLE 1

Comparison of Hemoglobin Measurement in Blood Collected on Treated and Untreated Filter Paper Blood spots from a single finger stick were collected onto a cellulose-based filter paper pre-treated with 3.8 mM (1×) EDTA, and a cellular filter paper left untreated. The filter paper used was a standard filter paper used in remote-site blood spot collection. The blood spots were allowed to dry overnight. Standard hemoglobin assays were then performed on five (5) replicates of samples collected from five different individuals.

Side-by-side comparison of the hemoglobin values for the 1× EDTA-treated and untreated filter paper, as determined by standard hemoglobin assay, showed the untreated filter paper to provide, overall, higher values for the hemoglobin measured in the blood. However, hemoglobin measurements in blood collected on the 1× EDTA-treated filter paper showed more precise measurement. The results of this experiment are shown in Table 1 below:

TABLE 1

| Sample No. | Untreated | | EDTA-treated | |
| --- | --- | --- | --- | --- |
| 1 | avg. | 234 | avg. | 219.6 |
|   | s.d. | 5.01 | s.d. | 6.65 |
|   | c.v. | 2.1% | c.v. | 3.0% |

TABLE 1-continued

| Sample No. | | Untreated | | EDTA-treated |
|---|---|---|---|---|
| 2 | avg. | 291.8 | avg. | 275.6 |
|  | s.d. | 9.86 | s.d. | 6.21 |
|  | c.v. | 3.4% | c.v. | 2.2% |
| 3 | avg. | 258.4 | avg. | 255.6 |
|  | s.d. | 10.83 | s.d. | 8.13 |
|  | c.v. | 4.2% | c.v. | 3.2% |
| 4 | avg. | 324.6 | avg. | 312.8 |
|  | s.d. | 25.98 | s.d. | 11.82 |
|  | o.v. | 8% | c.v. | 5.8% |
| 5 | avg. | 258.6 | avg. | 158.2 |
|  | s.d. | 11.12 | s.d. | 16.1 |
|  | c.v. | 4.3% | c.v. | 6.20% | avg. = average measurement of five assays
s.d. = standard deviation of five replicate sample measurements
c.v. = coefficient of variation of five replicate sample measurements The mean standard of deviation was more than 12.5 and a mean coefficient of variation of 4.4% for the untreated filter paper. The EDTA-treated filter paper yielded a mean standard of deviation of less than 10, and a mean coefficient of variation of about 4%. Thus, the EDTA treatment showed higher precision measurement of hemoglobin by standard assay procedures.

EXAMPLE 2
Hemoglobin Measurements in Simulated Aged Blood Samples

In this experiment, five blood samples from a finger stick from five individuals were collected onto filter paper pretreated with 7.7 mM (2x) EDTA and on untreated filter paper. The collected blood samples were heated to 45° C. for a period of about two days to simulate aging of the blood that can occur during transport of the sample from a remote collection site to a laboratory where analysis is performed. At least three replicates of each sample were subjected to hemoglobin analysis using a standard assay procedure. For purposes of a control, the "untreated" filter paper was absorbed with volume of distilled water equal to the amount of EDTA solution. The results of this experiment are shown in Table 2 below:

TABLE 2

| Sample No. | | 2X-EDTA-treated | | Untreated |
|---|---|---|---|---|
| 1 | avg. | 280 | avg. | 293 |
|  | s.d. | 9.46 | s.d. | 30.27 |
|  | c.v. | 3.4% | c.v. | 10.3 |
| 2 | avg. | 259 | avg. | 247 |
|  | s.d. | 8.52 | s.d. | 3.77 |
|  | c.v. | 3.3% | c.v. | 1.5% |
| 3 | avg. | 239 | avg. | 248 |
|  | s.d. | 7.48 | s.d. | 12.03 |
|  | c.v. | 3.1% | c.v. | 4.8% |
| 4 | avg. | 239 | avg. | 424 |
|  | s.d. | 4.11 | s.d. | 1.63 |
|  | c.v. | 1.7% | c.v. | 0.7% |
| 5 | avg. | 281 | avg. | 299 |
|  | s.d. | 12.57 | s.d. | 19.65 |
|  | c.v. | 4.5% | c.v. | 6.6% | avg. = average measurement of five assays for EDTA-treated filter paper and three assays untreated filter paper
s.d. = standard deviation of replicate measurements
c.v. = coefficient of variation of replicate measurements Overall, the 2x EDTA-treated filter paper showed the lowest hemoglobin measurements, but, more significantly, the highest precision, as indicated by the lowest standard deviation and coefficient of variation as compared to any of the treatments described in Examples 1 or 2 provided herein.

It should be understood that the examples and embodiments herein are for illustrative purposes only and various modifications or changes in light thereof will be suggested to persons skilled in the art and are to be included within the spirit and purview of this application and the scope of the appended claims.

What is claimed is:

1. A method for assaying a hemoglobin in a liquid biological sample, said method comprising:

providing a material for absorbing the biological sample comprising the hemoglobin, the material containing a chelating agent for preventing the liquid biological sample from coagulating;

applying the liquid biological sample to the chelating agent-containing material;

allowing the liquid biological sample to dry into a dried biological sample on the material;

eluting the dried biological sample from the material, whereby tile chelating agent facilitates elution of the dried biological sample from the material to improve the precision of the method; and assaying the hemoglobin in the eluted dried biological sample.

2. The method according to claim 1, wherein said step of allowing, the liquid biological sample to dry into a dried biological sample on the material is accomplished in a time period of at least approximately twenty-four hours.

3. The method according to claim 1, wherein the material is filter paper.

4. The method according to claim 3, wherein the filter paper is cellulose based.

5. The method according to claim 1, wherein the liquid biological sample is blood.

6. The method according to claim 5, wherein the chelating agent is citric acid.

7. The method according to claim 1, wherein the hemoglobin is a glycohemoglobin.

8. The method 7, wherein the glycohemoglobin is HbA1c.

9. The method according to claim 1, wherein the chelating agent is ethylenediamine tetra-acetic acid.

10. The method according to claim 9, wherein the liquid biological sample is blood and the ethylenediamine tetra-acetic acid is applied to the material in a quantity of at least 5 $\mu$g/20 $\mu$l of blood to prevent coagulation of the blood.

11. The method for assaying a hemoglobin in a liquid biological sample according to claim 6, wherein the liquid biological sample is blood and the ethylenediamine tetra-acetic acid is applied to the material in a quantity of at least 10 $\mu$g/20 $\mu$l of blood to prevent coagulation of the blood.

12. The method according to claim 1, wherein the chelating agent is present in a quantity sufficient to prevent coagulation of the liquid biological sample applied to the material.

* * * * *

UNITED STATES PATENT AND TRADEMARK OFFICE
CERTIFICATE OF CORRECTION

PATENT NO.    : 6,309,887 B1
DATED         : October 30, 2001
INVENTOR(S)   : Robert A. Ray It is certified that error appears in the above-identified patent and that said Letters Patent is hereby corrected as shown below:

Column 6,
Line 25, replace "tile" with -- the --,
Line 32, replace "allowing," with -- allowing --,
Line 47, insert -- according to claim -- after "method",
Line 55, replace "6" with -- 9 --.

Signed and Sealed this

Twenty-seventh Day of August, 2002

Attest:

JAMES E. ROGAN
Attesting Officer    Director of the United States Patent and Trademark Office